United States Patent [19]

Guldemond, deceased

[11] Plant 4,033

[45] Apr. 5, 1977

[54] GLADANTHERA GULDEMOND-CORNELIUS

[75] Inventor: Cornelius K. Guldemond, deceased, late of Ross Township, Kalamazoo County, Mich., by Myrta M. Guldemond, legal representative

[73] Assignee: Myrta M. Guldemond, Galesburg, Mich.

[21] Appl. No.: 601,480

[22] Filed: Aug. 4, 1975

[51] Int. Cl.[2] ..... A01H 5/00

[52] U.S. Cl. ..... Plt./85

[58] Field of Search ..... Plt./85

*Primary Examiner*—Robert E. Bagwill

*Attorney, Agent, or Firm*—Woodhams, Blanchard and Flynn

[57] ABSTRACT

A new and distinct member of the Iridaceae family characterized by a unique combination of the characteristics of the Gladiolus and the *Acidanthera murielae*, namely a flower of the Gladiolus, the drooping characteristic of the flower of the Acidanthera, and the fragrance of the Acidanthera.

1 Drawing Figure

This invention relates to a new and distinct member of the Iridaceae family, hereinafter referred to as a Gladanthera Guldemond-Cornelius plant.

This new Gladanthera Guldemond-Cornelius plant was originated by crossing the common Gladiolus with an *Acidanthera murielae* by using the pollen from the *Acidanthera murielae* and applying it to the end of the stigma of the Gladiolus.

The improved variety resulting from this breeding is evidenced by the following unique combination of characteristics which are outstanding therein and which distinguish the new variety from its parents, as well as from other varieties.

First: A large flower of the Gladiolus type and having the fragrance of the *Acidanthera murielae* and also some of the droop of the *Acidanthera murielae*.

Second: The fragrance ranges from mild to strong.

As a result, the long desire for a fragrant flower having a Gladiolus appearance is now a reality.

In addition to these major characteristics the variety is also endowed with the following characteristics:

1. Good bud count
2. Stem freedom from crooking
3. Admirable and consistent growth habits
4. Excellent propagative powers The plant has been asexually reproduced by cormels through several generations in Michigan and succeeding generations have established that the distinguishing characteristics of the variety held true. By natural increase from cormels through several generations its color and other characteristics have proven to be permanently fixed.

The accompanying drawing shows a typical specimen of a flower spike of the new variety, with the flowers in varied stages of growth. Some are shown as partially opened buds and others as fully opened buds. The colors depicted are as nearly true as is possible to achieve in this type of reproduction and the colors set forth below are with reference to the Pantone Matching System.

The following is a detailed description of the new genus.

PLANT

Growth: Healthy, vigorous and consistent; excellent propagator.

Blooming habit: Under normal conditions the first bloom appears approximately 8 to 10 weeks after planting in the Southwestern Michigan climate with 6 to 9 florets showing color at one time. In the Southwestern Michigan climate, the planting occurs about the end of May, first part of June.

Stems:

*Form.*—Tall and straight.

*Diameter at base.*—About ¾ inch.

*Color at base.*—Green.

Foliage: Above the ground they are medium green. The average leaf is one and three-quarters inch wide at the base, grows 12 to 18 inches long, tapers gracefully to a point and droops artistically from the spot where the taper begins.

Disease resistance: The variety has been found to be unusually resistant to the usual Gladiolus plant diseases of a bacterial, viral or fungoid genesis.

Corms: Mature corms are plump and high-crowned with paperlike husks which are straw colored at the point of their attachment, continuing straw colored to near the top. The corm color, exclusive of husks, is generally yellow, namely between and including Pantone Nos. 106 to 107. Corms ½ inch or greater in diameter will produce flowering spikes. There is no frost hardiness of the corms.

FLOWER

Spike:

*Form and size.*—Tall and straight 30 to 36 inches, with bloom spike regularly carrying eight to 12 buds with the flowers being somewhat tubular and funnel-shaped enlarging upwardly, then drooping a little, the amount of droop of the flower being about halfway between the uncrossed Gladiolus and Acidanthera. This is a new characteristic of the new Gladanthera Guldemond. Thus, the new Gladanthera Guldemond has picked up some of the characteristics of both parent plants. When observed in Northern Virginia under hot, dry conditions, most of the flowering spikes were compound, with from two to five spikelets, each having from four to ten blossoms.

Bud:

*Size.*—About 2 inches long when opening.

*Opening.*—On first blooming 3 or 4 buds open with 2 or 3 a day opening thereafter.

Flower:

*Size.*—Individual florets average about 2¾ to 3½ inches in diameter.

*Keeping qualities.*—The flowers keep well and open exceptionally well from tight buds.

Petals:

*Shape.*—Somewhat rounded at the tips and flat.

*Size.*—Upper petals — about 2 inches wide. Lip petals – about 1 to 1½ inches wide.

*Fragrance.*—The same as but not quite as strong as the Acidanthera. If the temperature is generally 80° F or greater over several weeks period of time at the time the flowers begin to bloom, little if any fragrance will be noted. The flowers become most fragrant when the evening temperatures reach 45° to 50° F and the day time temperatures do not exceed 70° to 75° F.

*Color.*—Generally white, opening color on first day of Pantone No. 100 turning as soon as it becomes fully open to white. The throat tapers from white to Pantone Magenta, namely between and including Pantone Nos. 240 and 241 at the throat base.

REPRODUCTIVE ORGANS

Stamens:

*Color.*—White.

Pistils:

*Color.*—Cream.

GROWTH

Locality where grown and observed: Galesburg, Mich.

Propagation: Holds its distinguishing characteristics through propagations from cormels.

It can be seen that this variety is unique in its fragrance and the drooping characteristics of the flowers.

The embodiments of the invention in which an exclusive property or privilege is claimed is defined as follows:

1. A new and distinct variety of plant in the Iridaceae family, substantially as herein shown and described, characterized particularly as to novelty by the unique combination of the characteristics of the common Gladiolus and the *Acidanthera murielae*, namely the flower of a Gladiolus, the drooping characteristic of the flower of the *Acidanthera murielae*, and the fragrance of the *Acidanthera murielae*.

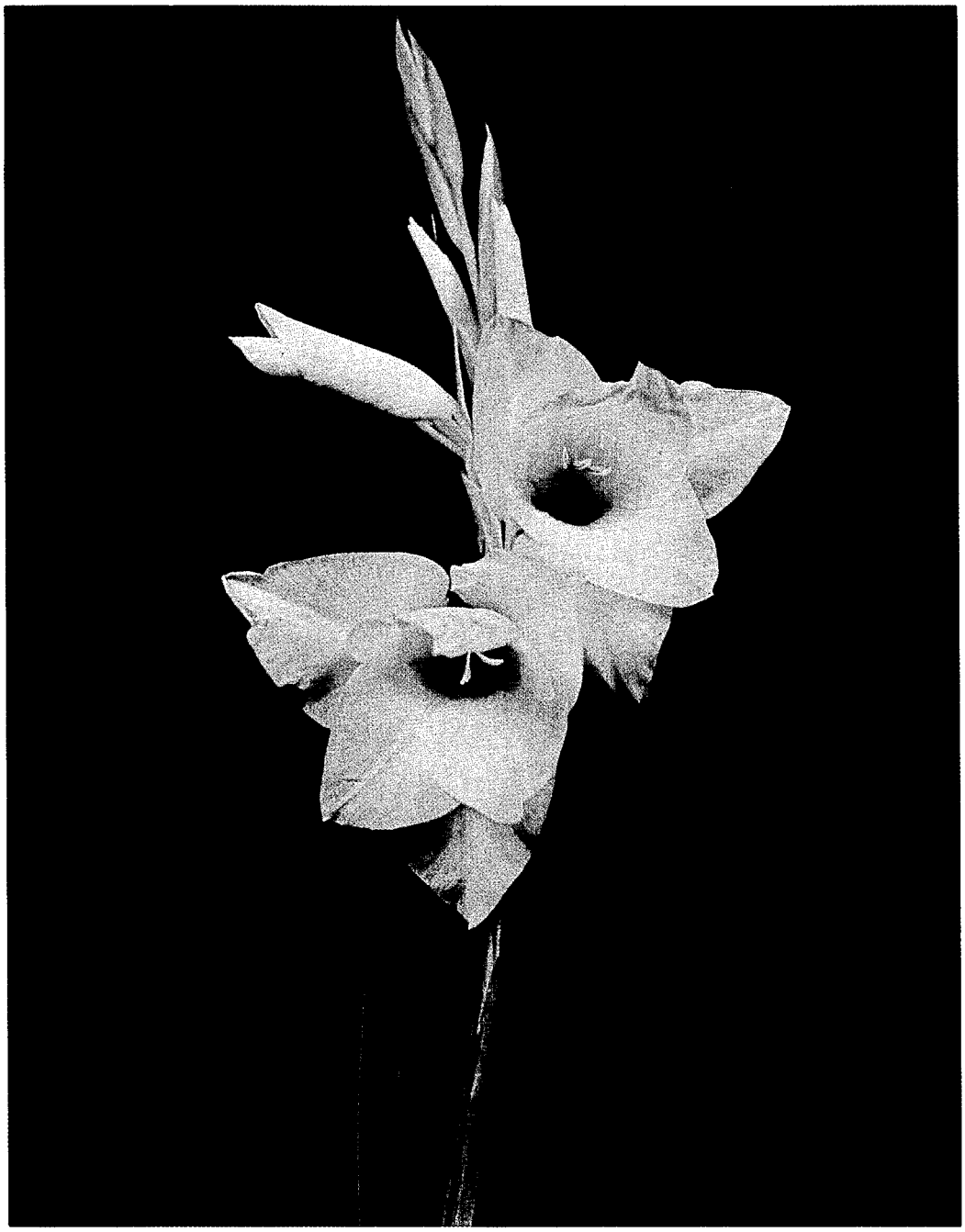

* * * * *